US00PP24725P3

(12) United States Plant Patent
Carruth

(10) Patent No.: US PP24,725 P3
(45) Date of Patent: Aug. 5, 2014

(54) GRANDIFLORA ROSE PLANT NAMED 'WEKEBTIDERE'

(50) Latin Name: *Rosa hybrida*
Varietal Denomination: WEKebtidere

(71) Applicant: Early Morning LLC, Pomona, CA (US)

(72) Inventor: Thomas F. Carruth, Altadena, CA (US)

(73) Assignee: Early Morning LLC, Pomona, CA (US)

( * ) Notice: Subject to any disclaimer, the term of this patent is extended or adjusted under 35 U.S.C. 154(b) by 72 days.

(21) Appl. No.: 13/694,321

(22) Filed: Nov. 19, 2012

(65) Prior Publication Data

US 2014/0143913 P1 May 22, 2014

(51) Int. Cl.
*A01H 5/00* (2006.01)

(52) U.S. Cl.
USPC ..... Plt./130

(58) Field of Classification Search
USPC ..... Plt./130, 138, 132
See application file for complete search history.

(56) References Cited

U.S. PATENT DOCUMENTS

PP18,850 P2 5/2008 Carruth

*Primary Examiner* — Kent L Bell
(74) *Attorney, Agent, or Firm* — McKee, Voorhees & Sease, P.L.C.

(57) ABSTRACT

A new variety of Grandiflora rose suitable for garden decoration, having flowers of deep velvet purple coloration.

1 Drawing Sheet

Classification: The present invention relates to a new *Rosa hybrida* plant.

Variety denomination: The new plant has the varietal denomination 'WEKebtidere'.

BACKGROUND OF THE INVENTION

This invention relates to a new and distinct variety of Grandiflora Rose. It has as its seed parent the variety known as 'WEKsmopur' (U.S. Plant Pat. No. 18,850) and as its pollen parent the variety known as 'WEKrorobluni' (not patented).

SUMMARY OF THE INVENTION

Among the features which distinguish the new variety from other presently available and commercial rose cultivars known to the inventor are the following combinations of characteristics: its unusual deep velvet purple coloration, its excellent color stability throughout the life of the flower, its very double petalage and numerous petaloids and its strong citrus blossom to spicy fragrance. The plant has a bushy upright to slightly spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKebtidere' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKsmopur', by the following combination of characteristics: whereas 'WEKebtidere' bears very double flowers (about 80 to 96 petals), 'WEKsmopur' bears flowers with significantly lesser petalage (about 29 to 46 petals). The new variety is classified as a Grandiflora rose with a bushy upright to slightly spreading medium height growing habit (about 85 to about 105 cm. in height), whereas the seed parent is classified as a Floribunda rose with a rounded and compact significantly shorter growing habit (about 66 to about 80 cm. in height).

The new variety may be distinguished from its pollen parent, 'WEKrorobluni', by the following combination of characteristics: whereas 'WEKebtidere' bears very double flowers (about 80 to 96 petals) of deep velvet purple coloration, 'WEKrorobluni' bears double flowers of fuchsia magenta coloration with significantly lesser petalage (about 26 to 40 petals). The new variety is classified as a Grandiflora rose with a bushy upright to slightly spreading medium height growing habit (about 85 to about 105 cm. in height), whereas the pollen parent is classified as an Hybrid Tea rose with an upright significantly taller growing habit (about 120 to about 140 cm. in height).

COMPARISON WITH THE CLOSEST COMMERCIALLY AVAILABLE CULTIVAR

The closest commercially available cultivar to the new variety is the seed parent 'WEKsmopur' (U.S. Plant Pat. No. 18,850).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of October. Throughout this specification, color references and/ or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of October. Phenotypic expression may vary with environmental, cultural and climatic conditions, as well as differences in conditions of light and soil.

FLOWER

The new variety sometimes bears its flowers singly, usually in clusters of three to five or more per stem. Flowers may be borne in regular moderately rounded clusters on strong medium length stems (about 22 to about 36 cm.). Outdoors, the plant blooms abundantly and nearly continuously during the growing season. The flowers have a strong citrus blossom to spicy fragrance.

BUD

The peduncle is about 3.5 to about 4.8 cm. in length, of average caliper (about 0.3 to about 0.4 cm. in diameter), and usually erect. It is almost entirely smooth with few stipitate glands. Peduncle color is between 144A and 146B sometimes lightly suffused, especially on the side exposed to the sun, with near 185C.

Before the calyx breaks, the bud is about 1.3 to about 1.7 cm. in diameter at the widest point, about 1.8 to about 2.0 cm. in length, and pointed to moderately ovoid in shape. The surface of the bud bears some stipitate glands and few hairs, usually with slender mostly entire foliaceous parts extending beyond the tip of the bud about ½ or more of its length. Bud color is between 144A and 146B.

The sepals are about 2.9 to about 3.6 cm. in length and about 0.9 to about 1.2 cm. in width at the widest point. The outer surface color of the sepal is between 144A and 146B. The outer surface of the sepal is smooth and bears between 1 to 3 foliaceous appendages with some stipitate glands and few hairs. The inner surface color of the sepal is between 194C and 148C. The inner surface of the sepal is covered with fine wooly tomentum; sepal margins are lined with many stipitate glands and hairs.

The receptacle of the flower is of somewhat short length (about 0.4 to about 0.5 cm.) and average in caliper (about 0.6 to about 0.9 cm. in diameter). The receptacle is moderately flat to cup-shaped in form. Its surface is smooth with somewhat thick fleshy walls. The receptacle color is between 144A and 146B.

As the petals open (after the calyx breaks), the bud is about 1.8 to about 2.2 cm. in diameter at the widest point, about 2.4 to about 2.6 cm. in length, and slightly pointed to globular in form. The color of the under surfaces of the newly opened petals is between 59A and darker than 64A, usually irregularly washed with between 187A and darker than 71A. At the point where the petal attaches, there is a somewhat large zone of between 2D and 155C. The color of the upper surfaces of the newly opened petals is between 60B and 61A, usually heavily washed with between 187A and darker than 71A on the outer half of the petal. At the point where the petal attaches, there is a large zone of between 2D and 4D.

BLOOM

When fully open, the bloom ranges from about 7.9 to about 9.9 cm. in diameter. Petalage is very double with about 80 to 96 petals and numerous (about 26 to about 41) petaloids irregularly arranged. When partially open, the bloom form is moderately cupped to slightly globular and the petals are loosely spiraled to cupped with somewhat undulated petal edges slightly reflexed outward. When fully open, the bloom form is cupped and the petals are more cupped with petal edges more undulated to moderately reflexed outward.

PETALS

The substance of the petals is somewhat heavy and of medium thickness, with upper surfaces slightly shiny to velvety and under surfaces satiny. The outer petals are about 3.3 to about 3.9 cm. in length and about 2.8 to about 3.5 cm. in width at the widest point. The intermediate and inner petals are about 2.2 to about 3.0 cm. in length and about 1.5 to about 2.6 cm. in width at the widest point. Petal margins are usually entire.

The outer petals are broadly obovate to nearly round in shape with rounded apices. The intermediate and inner petals are narrowly obovate to broadly oblanceolate in shape with rounded to slightly irregular apices.

Petaloids are about 0.8 to about 2.0 cm. in length and about 0.6 to about 1.7 cm. in width at the widest point. Petaloids are irregular shaped narrowly oblanceolate with rounded apices.

NEWLY OPENED FLOWER

The under surface color of the outer petals is between 64B and 71A, usually irregularly washed with darker than 77A. The under surface color of the intermediate and inner petals is similar in coloration to the under surface of the outer petals with significantly less of the darker wash coloration. At the point where the petal attaches, there is a somewhat large zone of between 2D and 4D.

The upper surface color of the outer, intermediate and inner petals is between 64A and 71A, usually heavily washed with between 79B and darker than 71A on the outer half of the petal. At the point where the petal attaches, there is a moderately large zone of between 4D and 158B.

The under and upper surface colors of the petaloids are similar in coloration to the upper and under surfaces of the intermediate and inner petals.

The general tonality of the newly opened flower is between 64A and 71A, usually heavily washed with between 79B and darker than 71A.

THREE-DAY-OLD FLOWER

The under surface color of the outer petals is between 70A and 72A, usually irregularly washed with near 77A. The under surface color of the intermediate and inner petals is similar in coloration to the under surface of the outer petals with little to none of the darker wash coloration. At the point where the petal attaches, there is a somewhat large zone of between 155B and 155D.

The upper surface color of the outer, intermediate and inner petals is between 71C and 71B, usually heavily washed with between 79C and 77A on the outer half of the petal. At the point where the petal attaches, there is a moderately large zone of between 155B and 155A.

The under and upper surface colors of the petaloids are similar in coloration to the upper and under surfaces of the intermediate and inner petals.

The general tonality of the three-day-old flower is between 71C and 71B, usually heavily washed with between 79C and 77A.

On the spent bloom, the petals usually drop off cleanly and are not particularly affected by cold, hot, wet, or dry weather.

In October in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are few in number (average about 20) and are arranged regularly about the pistils; some are mixed with petaloids. The filaments are of moderately irregular length, somewhat short to medium (about 0.3 to about 0.6 cm.) most with anthers. Filaments are near 14D in color. The anthers are somewhat small to medium for the class and all open approximately at the same time. Anther color when immature is near 22C. Anther color at maturity is near 165A. Pollen is moderate and near 19D in color.

FEMALE REPRODUCTIVE ORGANS

Pistils vary in number (average about 35). The styles are mostly even and long in length (about 0.9 to about 1.1 cm.), somewhat thin to average in caliper, and moderately bunched. Stigma color is near 161D. Style color is near 2D often moderately suffused, mostly on the upper half, with near 45A. Ovaries are all enclosed in the calyx.

Hips have not been observed on this variety when grown in Pomona, Calif.

FOLIAGE

The compound leaves are usually comprised of three to five leaflets and are borne abundantly. The five-leaflet leaves are about 10.4 to about 12.6 cm. in length and about 7.1 to about 9.4 cm. in width at the widest point, moderately heavy to somewhat leathery in texture, and moderately glossy in finish on the upper side and matte in finish on the underside. The leaves have a pinnate venation pattern. The terminal leaflets are about 3.9 to about 5.9 cm. in length and about 3.1 to about 3.8 cm. in width at the widest point, shaped moderately oval to somewhat ovate with acute apices and moderately rounded bases. Their margins are usually simply serrate.

The upper surface color of the mature leaf is between 147A and 146A. The under surface color of the mature leaf is between 147B and 191A. The under and upper colors of the leaf veins on the mature leaf are similar in coloration to the upper and under surfaces colors of the mature leaf. The upper surface color of the young leaf is between 146A and 143A, sometimes lightly suffused with near 183B. The under surface color of the young leaf is between 138B and 144B, sometimes lightly suffused with near 183A. The under and upper colors of the leaf veins on the young leaf are similar in coloration to the upper and under surfaces colors of the young leaf.

The rachis is average to moderately heavy in caliper and smooth. The upper side is moderately grooved with some hairs and stipitate glands on the edges of the grooves. The under side of the rachis is smooth with few stipitate glands. The rachis color is near 146C on the under side and near 146B on the upper side.

The stipules are about 1.8 to about 2.6 cm. in length and of medium width (about 0.3 to about 0.4 cm.) with moderately long straight points that usually turn out at an angle of 45 degrees or more. The under surface color of the stipule is near 146A. The upper surface color of the stipule is near 147A.

The petiole is average to moderately heavy in caliper and smooth. The upper side is moderately grooved with some hairs and stipitate glands on the edges of the grooves. The under side of the petiole is smooth with few stipitate glands. The petiole is about 0.1 to about 0.2 cm. in length and about 0.1 to about 0.2 cm in width at the widest point. The petiole color is near 146C on the under side and near 146B on the upper side.

The plant displays an average degree of resistance to powdery mildew and rust as compared to other commercial varieties grown under comparable conditions in Pomona, Calif. known to the Inventor. The plant's winter hardiness and drought/heat tolerance are yet to be determined.

GROWTH

The plant has a bushy upright to slightly spreading medium height growing habit (about 85 to about 105 cm. in height and about 85 to about 105 cm. spread at the widest point), with full branching. It displays moderately vigorous growth and the canes are of medium caliper for the class (about 1.6 to about 2.3 cm. in diameter at the widest point).

The color of the major stems is between 146B and 146C. They bear few large prickles that are about 0.5 to about 0.8 cm. in length. The large prickles are almost straight and angled slightly downward with a medium length moderately narrow oval base; prickle color is between 165B and 166A. The major stem bears no small prickles.

The color of the branches is between 144A and 146B. They bear few large prickles which are of similar size and shape to the large prickles on the major stems; prickle color is near 160B. The branches bear no small prickles.

The color of the new shoots is between 144A and 146C sometimes lightly suffused with near 183C. They bear few large prickles which are of similar size and shape to the large prickles on the major stems; prickle color is near 160D usually lightly suffused with near 183D. The shoots bear no small prickles.

I claim:

1. A new and distinct Grandiflora rose plant of the variety substantially as described and illustrated herein.

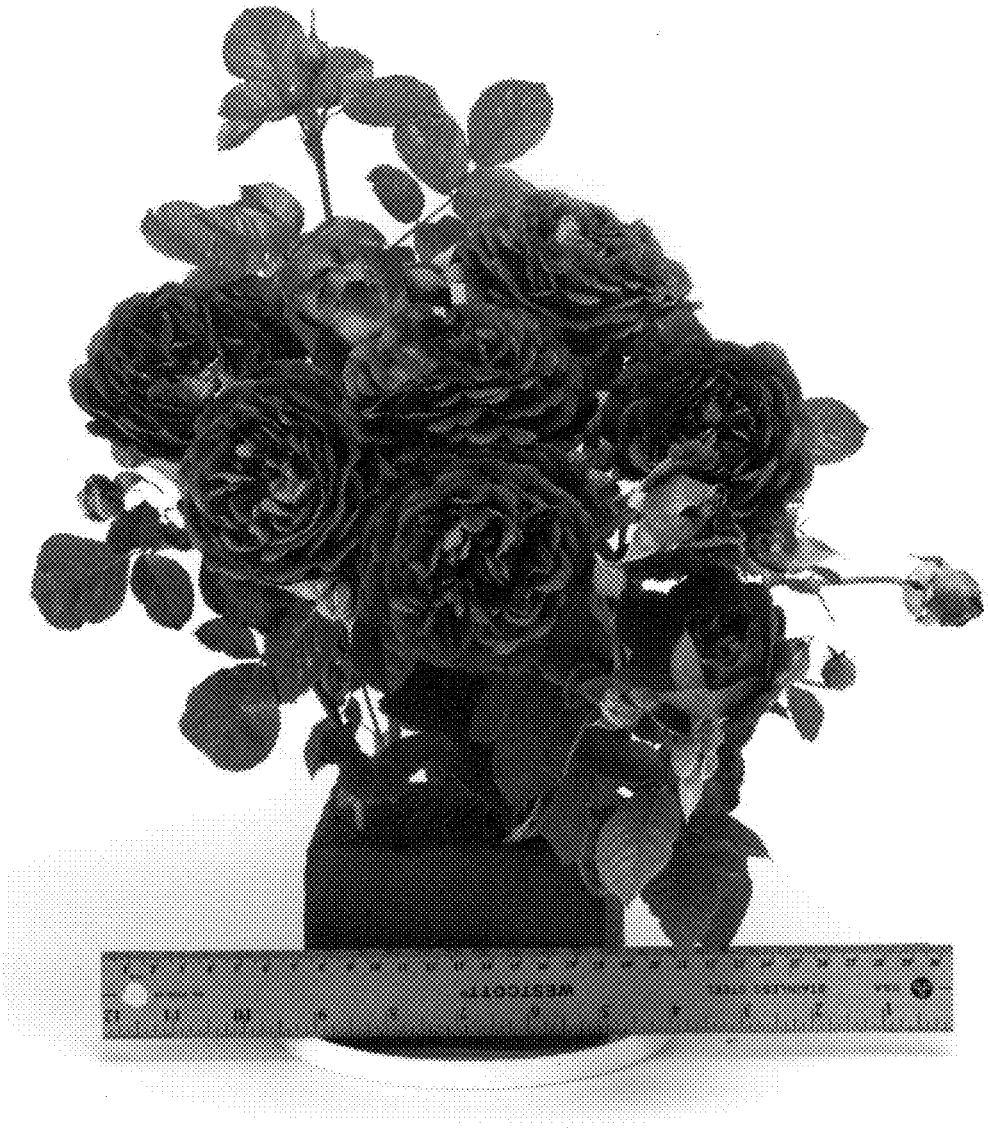

* * * * *